(12) United States Patent
Drummy et al.

(10) Patent No.: US 7,817,076 B2
(45) Date of Patent: Oct. 19, 2010

(54) MULTIPLE MODE DIGITIZATION SYSTEM FOR A NON-DESTRUCTIVE INSPECTION INSTRUMENT

(75) Inventors: Michael Drummy, North Reading, MA (US); Andrew Thomas, Westford, MA (US); Denys Laquerre, Quebec (CA); David Larochelle, Quebec (CA); Pierre Langlois, Quebec (CA); Steven Besser, Framingham, MA (US)

(73) Assignee: Olympus NDT, Waltham, MA (US)

( * ) Notice: Subject to any disclaimer, the term of this patent is extended or adjusted under 35 U.S.C. 154(b) by 39 days.

(21) Appl. No.: 12/192,369

(22) Filed: Aug. 15, 2008

(65) Prior Publication Data

US 2009/0045994 A1 Feb. 19, 2009

Related U.S. Application Data

(60) Provisional application No. 60/956,162, filed on Aug. 16, 2007.

(51) Int. Cl.
 *H03M 1/12* (2006.01)
(52) U.S. Cl. ...................... 341/155; 341/141
(58) Field of Classification Search ................ 341/155, 341/141, 111, 159, 120, 118
See application file for complete search history.

(56) References Cited

U.S. PATENT DOCUMENTS

| | | | |
|---|---|---|---|
| 5,515,048 A * | 5/1996 | Honda et al. | 341/55 |
| 6,611,774 B1 | 8/2003 | Zaccaria | 702/63 |
| 6,700,515 B2 * | 3/2004 | Asami | 341/120 |
| 6,836,230 B2 * | 12/2004 | Le Pailleur et al. | 341/141 |
| 6,985,831 B2 * | 1/2006 | Ito et al. | 702/188 |
| 7,176,816 B2 * | 2/2007 | Koerner et al. | 341/120 |
| 7,411,533 B2 * | 8/2008 | Posamentier | 341/122 |
| 7,541,958 B2 * | 6/2009 | Xu | 341/155 |
| 2006/0043303 A1 | 3/2006 | Safai et al. | 250/347 |
| 2006/0239389 A1 | 10/2006 | Coumou | 375/346 |

OTHER PUBLICATIONS

International Search Report dated Nov. 6, 2008.

* cited by examiner

*Primary Examiner*—Peguy JeanPierre
(74) *Attorney, Agent, or Firm*—Ostrolenk Faber LLP

(57) ABSTRACT

A multiple mode digitization system for a non-destructive inspection instrument which makes use of a multiplexing circuit and a single set of analog to digital converters to efficiently digitize analog test signals from a plurality of inputs. In the preferred embodiment, each of the analog to digital converters in the system is driven with an independent and separate clock signal, allowing for propagation delay compensation among the plurality of test signals as well as interleaved sampling such that custom sampling rates can be used for each input without the need for more than one clock frequency. In an alternate embodiment, phase adjustments on the sampling clocks are used only for interleave sampling, and digital filters are used to provide signal propagation delay compensation.

20 Claims, 14 Drawing Sheets

MULTIPLE MODE DIGITIZATION SYSTEM FOR A NON-DESTRUCTIVE INSPECTION INSTRUMENT

CROSS-REFERENCE TO RELATED APPLICATION

This application is based on and claims priority to U.S. Provisional Patent Application Ser. No. 60/956,162, filed on Aug. 16, 2007 and titled A MULTIPLE MODE DIGITIZATION SYSTEM FOR A NON-DESTRUCTIVE INSPECTION INSTRUMENT, the entire contents of which are hereby incorporated by reference.

BACKGROUND OF THE INVENTION

The present invention relates to non-destructive inspection (NDI) instruments, and more particularly to a multiple mode digitization system for said instruments which is well suited to accommodate multiple probe types.

Any discussion of the related art throughout this specification should in no way be considered as an admission that such art is widely known or forms a part of the common general knowledge in the field.

As digital signal processing electronics have grown smaller, more economical, and power efficient over the last several years, NDI instruments employing them have become increasingly more powerful and capable. Signal processing and data analysis once reserved for post inspection processes can now be performed in real time, and in some cases directly on handheld NDI instruments. Ultrasonic phased array systems, for example, can now be realized in small, portable instruments.

This dramatic increase in signal processing power has led to a new generation of NDI instruments. Making use of state of the art digital signal processing technology and techniques, a single compact NDI instrument can be realized which performs multiple inspection functions each of which requiring a separate input time and instrument mode—for example, but not limited to, an instrument which can function with a lower bandwidth array probe as well as a higher bandwidth, high dynamic range single element probe. Despite these advances in digital signal processing technology, however, a new design limitation has been encountered.

NDI probes with multiple sensor elements—that is to say probes which provide a plurality of individual signals to the instrument—such as array probes require multiple analog to digital converters to process all of the signals in parallel. While numerous post processing and multiple pulser and receiver firing methods (combining the results of a number of iterative measurements) can be used to reduce the number of analog to digital converters required in the digitization system of such an NDI instrument, simultaneous sampling of all signals is often required for real time signal analysis—such as that which is becoming increasingly more accessible through the improvement of digital signal processing technology. Despite the increased cost and size of such instruments, there exists an increasing need for systems which provide a dedicated analog to digital converter for each analog signal in a given probe.

Adding a second or third probe input to such an NDI instrument can further increase the number of analog to digital converters required. As the multiple probe inputs will likely have different numbers of sensor elements, bandwidth needs, and sampling rate requirements, simply reusing the existing analog to digital converters becomes problematic. While adding more and more analog to digital converters to the digitization system of an NDI instrument is certainly possible, it can quickly become impractical, as the size, cost, and power requirements of the instrument grow to accommodate the additional circuitry. Although digital signal processing technology has reached a point to allow for a multiple input/multiple mode NDI instrument, without a more efficient digitization system, such an instrument will be overly large, impractical, and not price competitive.

Accordingly, it would be advantageous to provide a digitization system for a NDI instrument which could accommodate multiple inputs without the need for a dedicated set of analog to digital converters on each input. Further, it would be advantageous if this digitization system were well suited for use with multiple input types, such as, but not limited to, array probes, single element probes, and the set of analog signals generated through a high bandwidth, high dynamic range probe receiver circuit such as the one disclosed in US 2007-0084288 by Thomas (incorporated herein by reference). It would also be advantageous if this digitization system were well suited to compensate for signal propagation delays experienced by the analog signals prior to digitization. It would further be advantageous if this digitization system were able to provide different sampling rates for each input without the need for multiple clock frequencies.

SUMMARY OF THE DISCLOSURE

It is the object of the present disclosure to overcome the problems associated with prior art. This is attained by introducing the multiple mode digitization system of the present disclosure. The digitization system of the present disclosure is comprised of at least one multiplexing block, one set of analog to digital converters which can be used for all inputs, and a phase adjuster to phase adjust the digitized signals relative to each other in steps less than the sample period.

Each input to the digitization system will be comprised of at least one analog signal. These signals—or set of signals in the likely case that an input is comprised of a plurality of analog signals—are provided to the set of analog to digital converters through the multiplexing block. In the preferred embodiment, each analog to digital converter is driven with a unique, independent clock allowing for small phase adjustments to be made to compensate for any signal propagation delays the analog signals experience prior to reaching the analog to digital converters. In one alternate embodiment, a plurality of programmable digital finite impulse response (FIR) filters is used to phased delay the test signals after digitization to correct for this signal propagation delay. In some cases, analog input signals will be connected to multiple analog to digital converters such that interleaved sampling can be realized through careful phase adjustments of the individual clock signals driving the analog to digital converters. In this way, higher sample rates can be achieved for certain inputs without the need for multiple clock frequencies.

Accordingly it is the object of the present disclosure to provide a digitization system for use with a non-destructive inspection instrument which can accommodate multiple inputs without the need for a unique set of analog to digital converters for each input.

It is also the object of the present disclosure that this digitization system be suitable for use with multiple input types, such as, but not limited to, array probes, single element probes, and the set of analog signals generated through a high bandwidth, high dynamic range probe receiver circuit such as is disclosed in US 2007-0084288 by Thomas.

It is further an object of the present disclosure that this digitization system be well suited to compensate for signal propagation delays experienced by the analog test signals prior to digitization.

It is also an object of the present disclosure that this digitization system be able to provide multiple sampling rates without the need for multiple clock signal frequencies.

Other features and advantages of the present invention will become apparent from the following description of the invention that refers to the accompanying drawings.

DETAILED DESCRIPTION

Figure 1:
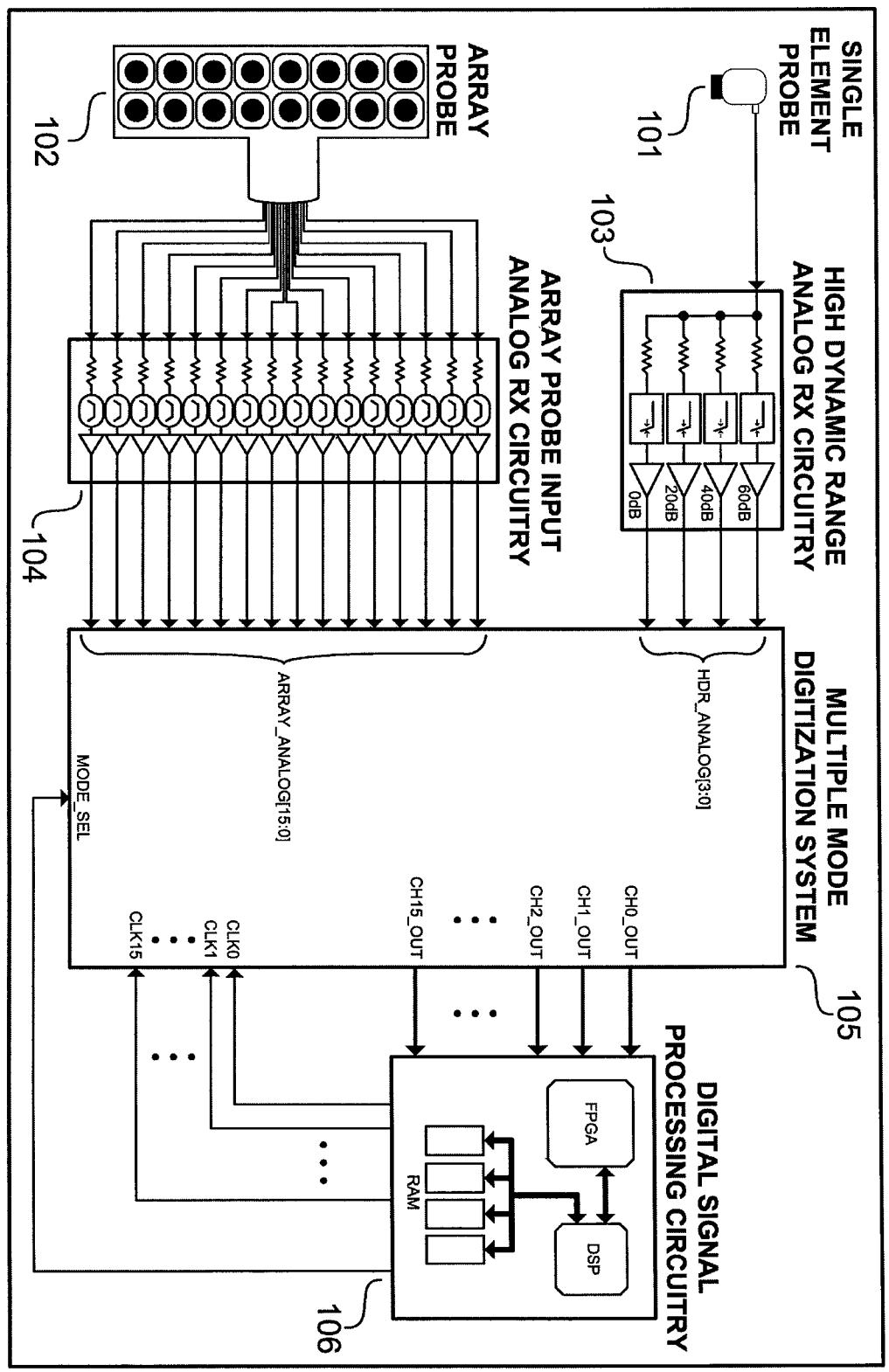
FIG. 1 is a block diagram of a typical non-destructive inspection (NDI) instrument using the multiple mode digitization system of the present disclosure.

FIG. 1 illustrates the block diagram of a typical non-destructive inspection (NDI) instrument which makes use of the digitization system of the present disclosure. In this case two different probe types are used with the instrument: a single element probe 101 and a multi-element array probe 102. Both probe types have different uses within a NDI process which should be well-known to those skilled in the art and are coupled to the instrument electronics through separate dedicated connectors.

The raw analog signals received from each probe are driven through an analog circuit block unique for each probe type. The signal received from the single element probe 101 is driven into a high dynamic range analog receiver circuit 103. This block works in a manner similar to that described in US 2007-0084288 by Thomas, the contents of which are incorporated herein by reference.

Figure 14:
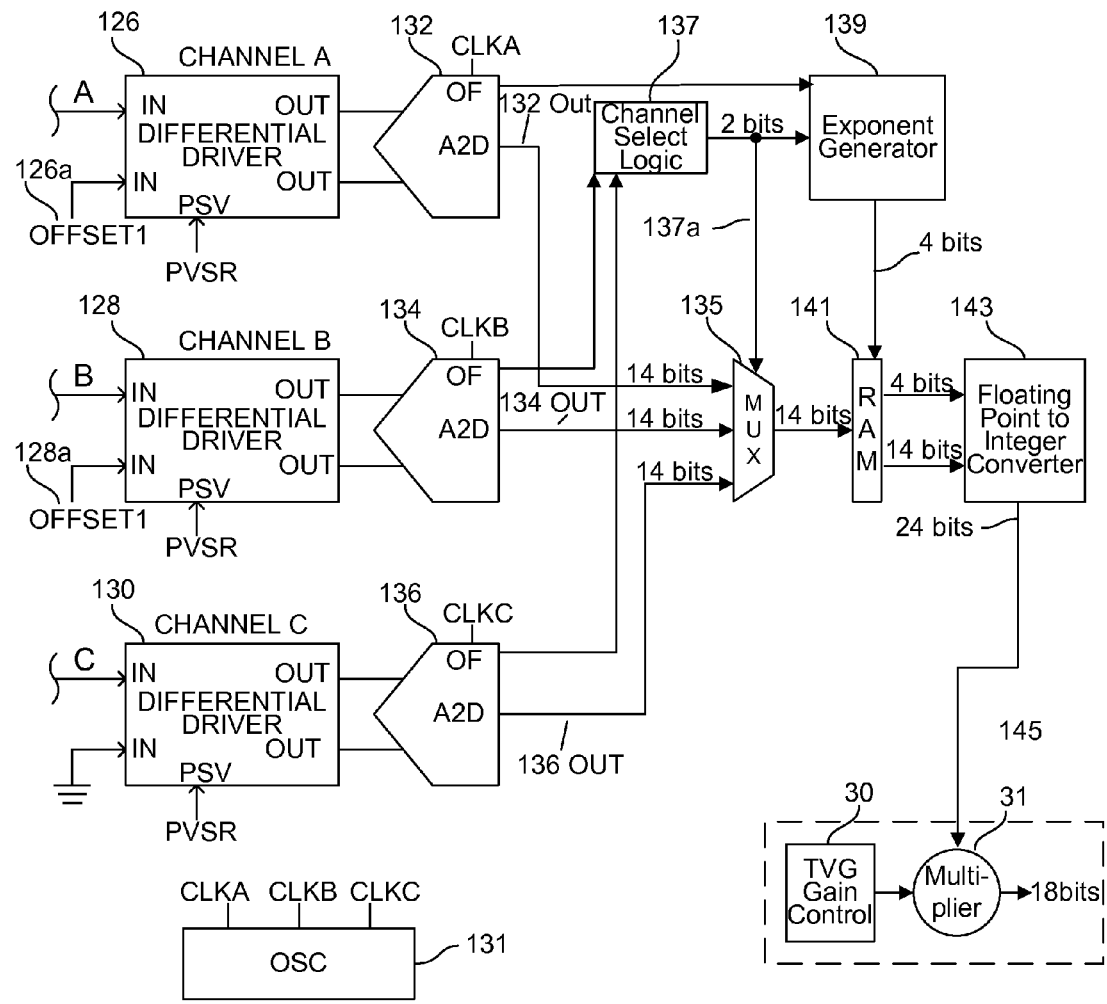
FIG. 14 is a diagram of a high dynamic range circuit.

Referring to FIG. 14, the A/D converters 132, 134 and 136 of the three channels are 14 bit, high speed converters for which sample timing is provided by the sample clocks CLKA, CLKB, CLKC derived from a 100 MHz oscillator block 131 using respective delay control elements contained within a FPGA circuit.

Each channel is sampled by one of three substantially identical A/D converters 132, 134, 136.

Channel Select Logic circuit 137 and the overflow signal from A/D converter 132 are connected to an Exponent Generator circuit 139. This circuit 139 calculates the exponent to go with the selected A/D converter data in RAM 141. A floating point conversion circuit 143 effectively adds bits of precision to the A/D conversion for small signals, while maintaining the range capacity for large signals. The floating point converter 143 also reduces the number of bits the sample data RAM requires.

The scaling is such that the maximum gain channel (C) has a resolution that is 32 times higher than the mid-gain channel (B), and 1024 times higher than the minimum gain channel (A). The higher resolution channels are monitored for data overflow, and the channel that has the highest resolution data without overflow is selected as the output. The selected outputs are merged to produce a seamless stream of output data.

Figure 4:
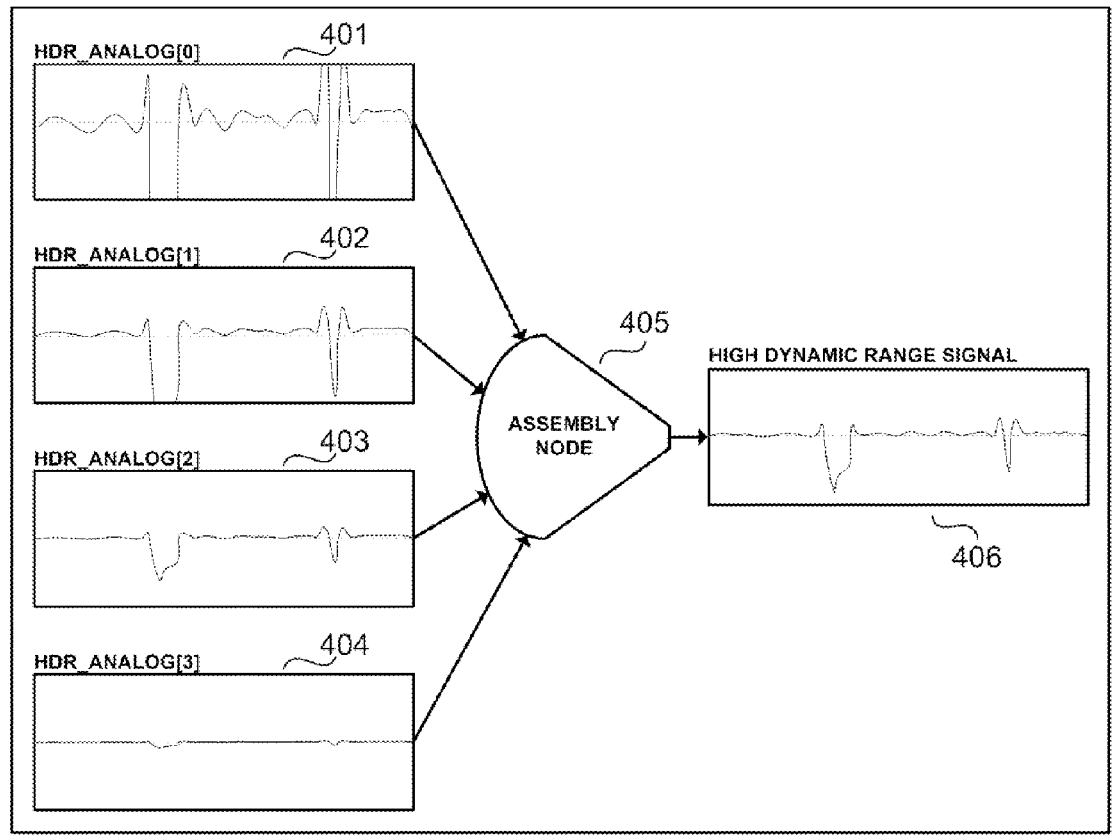
FIG. 4 is a diagram briefly illustrating methods of the high dynamic range circuit.

The analog signal received from the single element probe 101 is driven through four parallel filter and gain stages, resulting in four new analog signals, each a carefully filtered and amplitude scaled version of the original signal. Each of these new signals must be digitized separately in real time and driven into the digital signal processing (DSP) circuitry 106 where they are combined to form a single high dynamic range signal as taught by Thomas. This process is illustrated in FIG. 4 and discussed in detail below.

The analog input signals from the array probe 102 are driven through a separate analog block 104. Each signal is individually filtered and buffered prior to digitization to improve signal quality. In the exemplary instrument depicted in FIG. 1, the array probe contains sixteen elements, which result in sixteen separate analog signals, each of which must be digitized separately in real time and driven into the DSP circuitry 106 for analysis.

The multiple mode digitization system of the present disclosure 105 is responsive to both sets of analog signals (the four signals provided by the high dynamic range analog circuitry 103 and the sixteen signals provided by the array input analog receiver circuitry 104) and digitizes one set as selected by the MODE_SEL input (controlled by the DSP circuitry 106). The clock inputs (which drive the individual analog to digital converters) to the digitization system 105 are generated by the DSP circuitry 106 and in the preferred and first alternate embodiment can be phase adjusted to compensate for analog circuitry propagation delays between each of the analog signals. It will be shown in the disclosure of the second alternate embodiment that a plurality of digital filters can also be used for this propagation delay compensation operation, significantly reducing the number of independent clock signals required. As will be shown in detail below, the DSP circuitry 106 can also phase shift each clock signal up to 360 degrees to allow interleaved sampling between the analog to digital converters. In the preferred embodiment, the multiple mode digitization system of the present disclosure 105 provides sixteen digitized signals to the digital signal processing block 106 for further processing and analysis.

Although FIG. 1 and the majority of the subsequent figures describe an NDI instrument with two inputs, the multiple mode digitization system of the present disclosure is not limited in this regard. Indeed, it should become apparent from the following discussion that the methods of the present disclosure can be used to realize a plurality of digitization systems which can accommodate a variety of probe inputs and configurations. Similarly, it should be noted that the type and resolution of the analog converters used in the methods of the present disclosure are not specific to the methods of the present disclosure. Indeed, the selection of said analog to digital converters rests dependant only on the design constraints of the NDI instrument in question.

Figure 2:
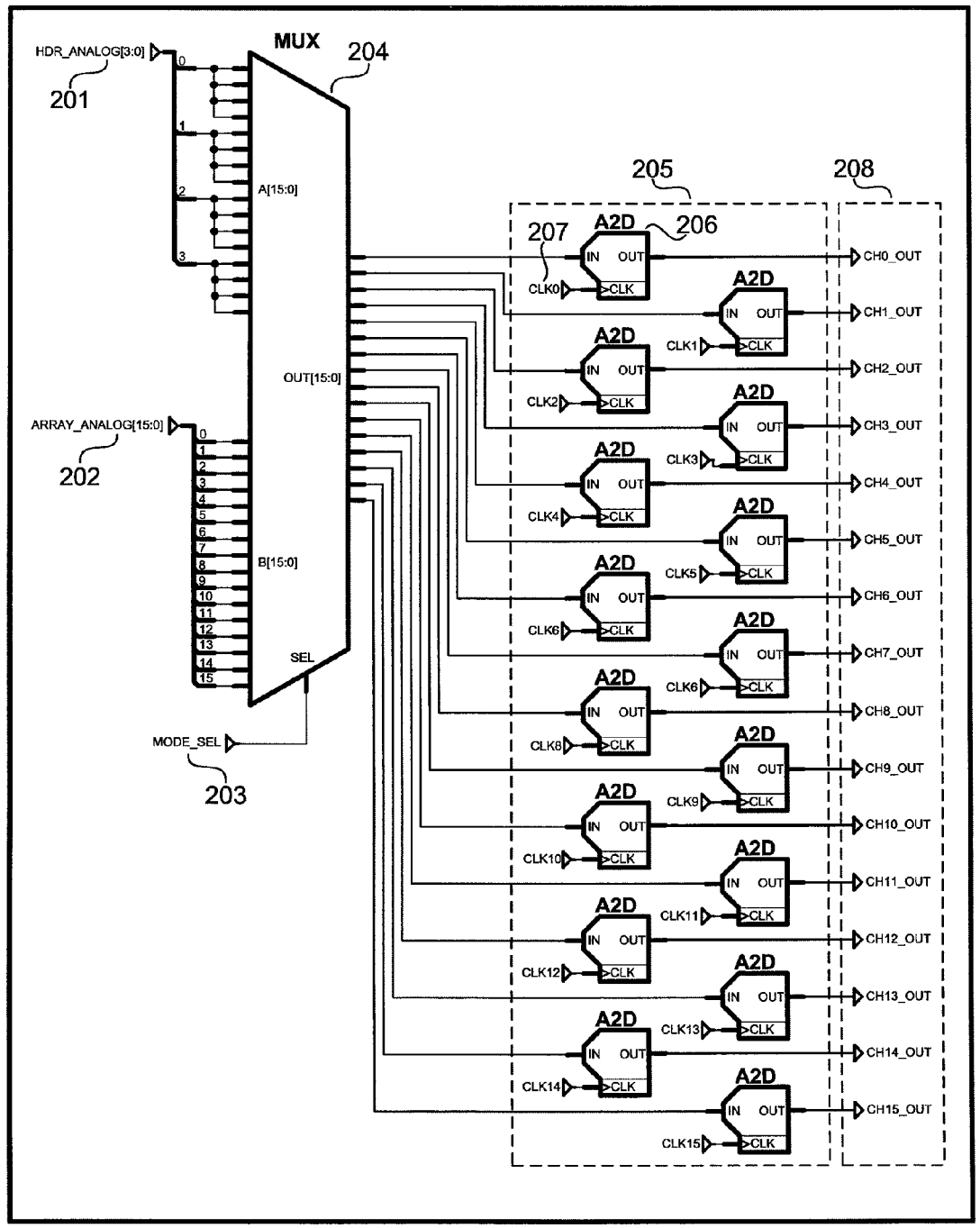
FIG. 2 is a block diagram of the preferred embodiment of the multiple mode digitization system of the present disclosure.

FIG. 2 illustrates the preferred embodiment of the multiple mode digitization system of the present disclosure in detail. The analog signals received from the different probe inputs are brought in as HDR_ANALOG[3:0] 201 (corresponding to the four analog signals generated from the single element probe 101 in FIG. 1) and ARRAY_ANALOG[15:0] (corresponding to the sixteen analog signals generated from the array probe 102 in FIG. 1). Both sets of signals are driven into a sixteen channel multiplexer 204, and one set subsequently provided to the multiplexer's 204 outputs dependant on the setting of the select control, MODE_SEL 203.

In the preferred embodiment, each of the four analog signals from the single element probe (HDR_ANALOG[3:0]) 201 is wired into the sixteen channel multiplexer 204 four times, such that each signal is provided to four different analog to digital converters 206 when the single element probe input 201 is selected by the MODE_SEL control 203. Conversely, each of the sixteen analog signals from the array probe (ARRAY_ANALOG[15:0]) 202 is wired to one of the sixteen channel multiplexer's 204 inputs such that each analog signal is provided to one analog to digital converter when the array probe mode is selected.

Each of the analog to digital converters 206 in the analog to digital converter bank 205 is driven with its own separate and independent clock signal 207. The sixteen clock signals 207 are all driven at the same frequency, however the phase of each clock signal can be adjusted within 360 degrees, providing two distinct advantages critical to the digitization system of the present disclosure. First, the phase of the sixteen clock signals 207 can be delayed in significantly small steps—time delay steps which are less than the sample period—to compensate for the plurality of signal propagation delays experienced by the analog signals as they were processed through the analog sections of the instrument. This signal propagation delay compensation is used for both modes (single element probe mode and array probe mode) and ensures that all sixteen differential pairs of digitized signals 208 provided by the bank of analog to digital converters 205 will be precisely phase aligned and ready for processing and analysis.

Figure 6A:
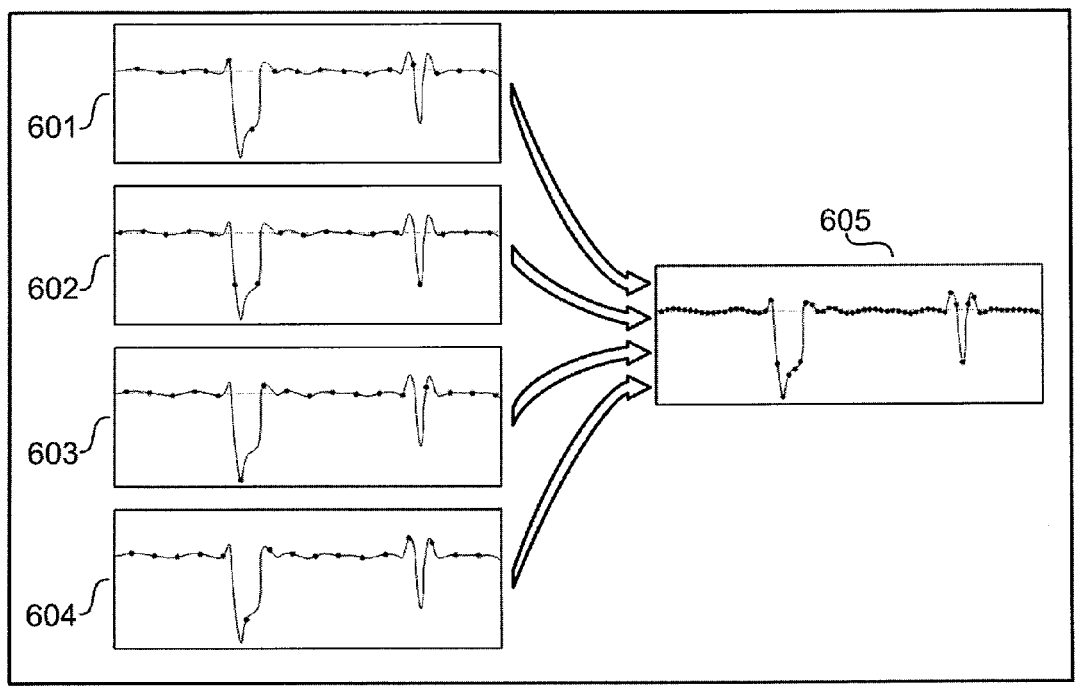
FIGS. 6A-6B are diagrams which graphically illustrate the interleaving sampling process as used in the preferred embodiment and the alternate embodiments respectively.
Figure 7:
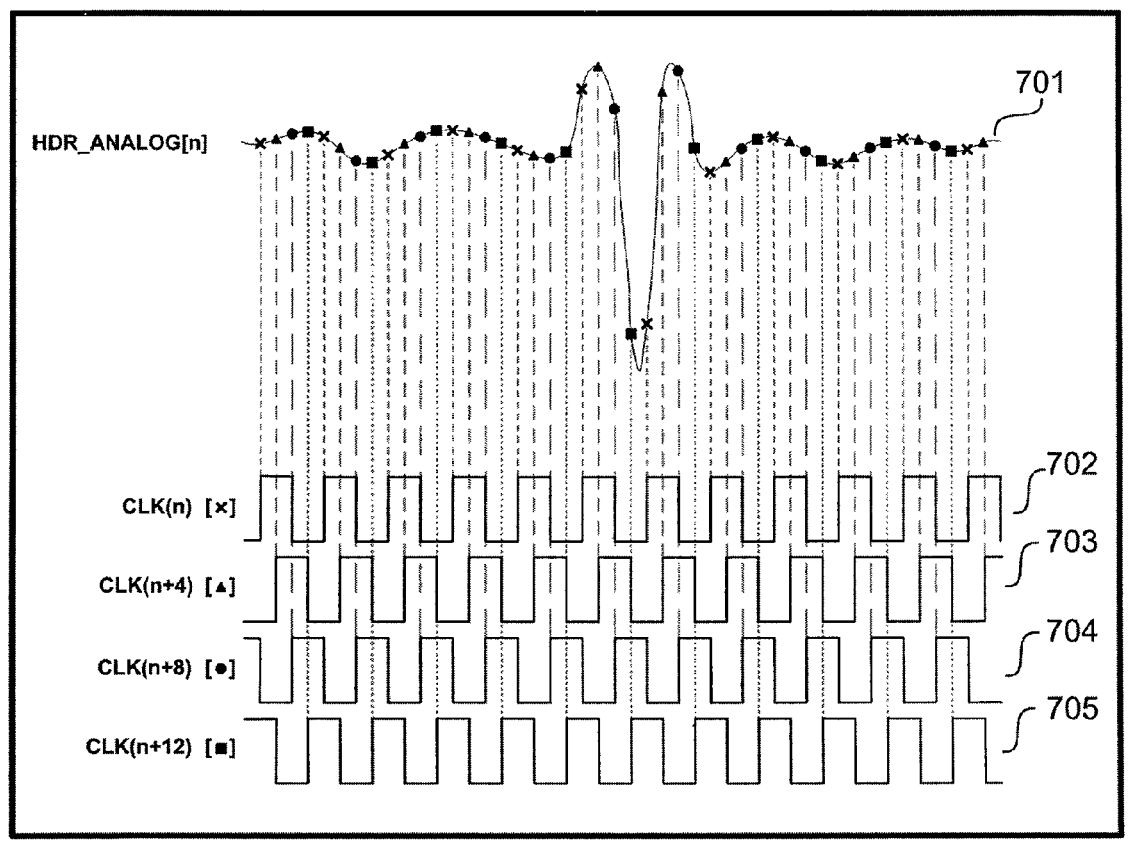
FIG. 7 is a timing diagram illustrating the interleaving sampling process as used in the preferred embodiment.

The second advantage is used with the single element probe mode (when the HDR_ANALOG[3:0] input 201 is selected by the MOD_SEL control 203). After the signal propagation compensations have been made—by making fine adjustments to each clock signal's phase—each of the clock signals 207 can be further adjusted in large steps to allow interleaved sampling between the different analog to digital converters 206. In the preferred embodiment of the present disclosure, the sixteen clock signals are driven at four different phases, 90 degrees apart, such that each of the four original analog signals (HDR_ANALOG[3:0]) 201 is sampled four times for each clock cycle. By combining the four sets of sampled digital data produced for each analog signal, an effective sampling rate is achieved which is four times the frequency of the clock signals 207. This process is illustrated in FIGS. 6A and 7 and discussed in detail below.

Figure 3:
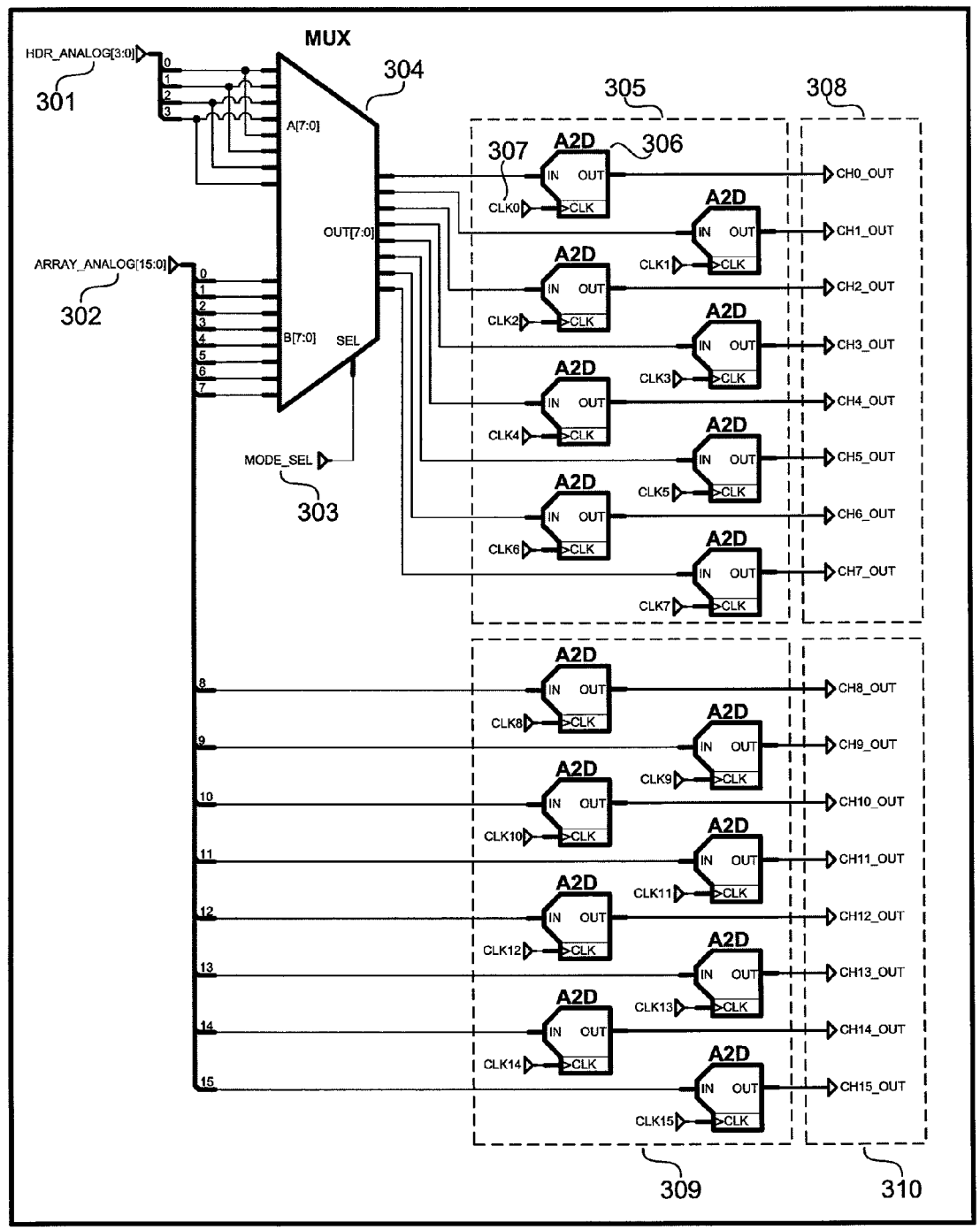
FIG. 3 is a block diagram of a first alternate embodiment of the multiple mode digitization system of the present disclosure.

FIG. 3 illustrates a first alternate embodiment of the multiple mode digitization system of the present disclosure. In this embodiment, an eight channel multiplexer 304 is used to select between the four analog signals generated from the single element probe (HDR_ANALOG[3:0]) 301 and the sixteen analog signals generated from the array probe (ARRAY_ANALOG[15:0]) 302. Each of the four signals from the single element probe (HDR_ANALOG[3:0]) 301 is driven into the eight channel multiplexer 304 twice, such that when the single element probe mode is selected, each of the four analog signals will be provided to two analog to digital converters 306.

As in the preferred embodiment, each of the sixteen analog to digital converters 306 is driven with a separate and independent clock signal 307. However, when the single element probe mode is selected in this embodiment, only eight of the sixteen analog to digital converters 306 (those contained in the first bank 305) are used. The remainder of the analog to digital converters 306 (those contained in the second bank 309) are only used in the array probe mode; therefore, bank 309 is kept in a low power or power off mode when not in use by means of control signals (not shown).

Figure 6B:
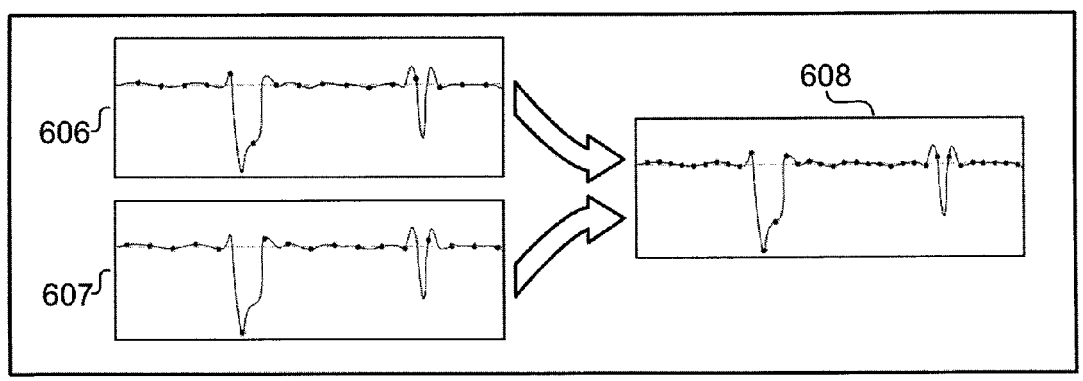
Figure 8:
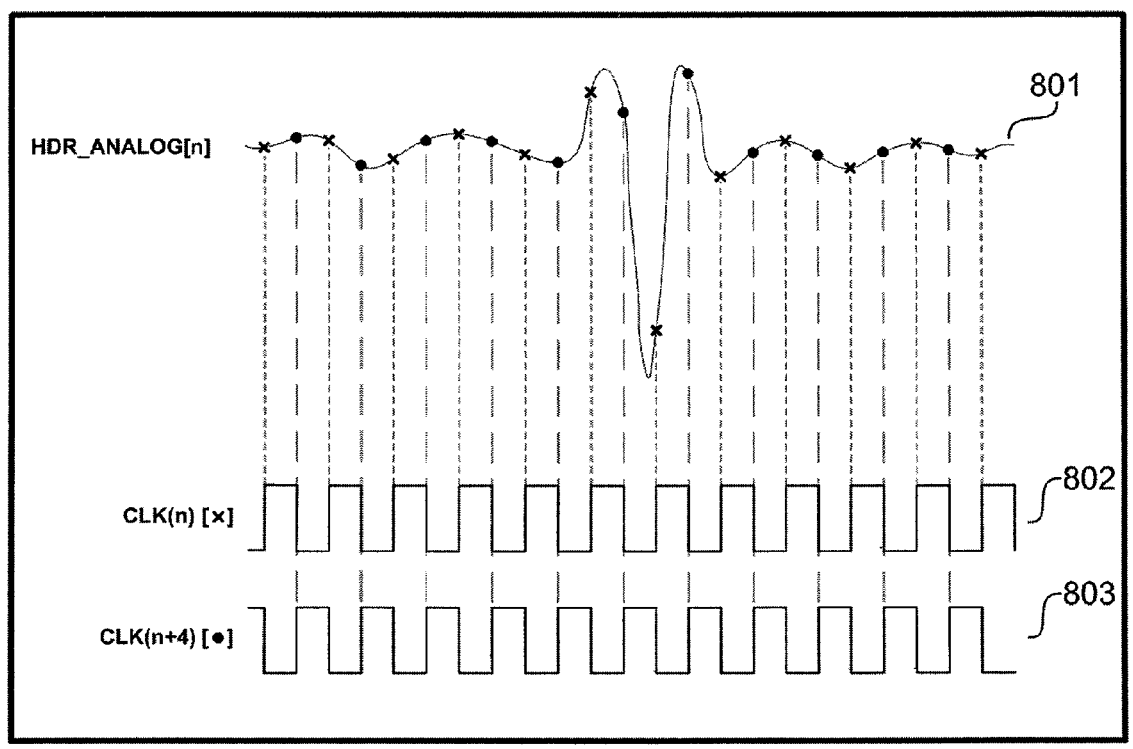
FIG. 8 is a timing diagram illustrating the interleaving sampling process as used in the alternate embodiments.

The signal propagation delay compensation adjustments are made in both modes (single element mode and array probe mode) as described in the preferred embodiment. In addition, when in the single element mode, the eight clock signals 307 contained in the first analog to digital converter bank 305 are driven with two coarse phase adjustment settings, 180 degrees apart, such that each of the original analog signals from the single element probe input (HDR_ANALOG[3:0]) 301 is sample twice for each clock cycle. By combining the two sets of sampled digital data produced for each analog signal, an effective sampling rate is achieved which is twice the frequency of the clock signals 307. This process is illustrated in FIGS. 6B and 8 and discussed in detail below.

It should be noted that while the preferred embodiment and the first alternate embodiment presented in FIGS. 2 and 3 respectively describe a multiple mode digitization system designed to function within a specific NDI instrument (namely one with exactly two inputs: a single element, four channel high dynamic range input and a sixteen element array probe input), the present disclosure is not limited in this regard. Indeed, it should be obvious from the preceding discussion of both FIGS. 2 and 3, that the methods of the present disclosure can be used to realize a plurality of multiple input digitization systems well suited for use in an NDI instrument, each with varying numbers and configurations of inputs and accommodating a variety of signal widths (the number of analog signals per input), sampling rate requirements, and input selection requirements.

FIG. 4 is provided as a reference to briefly illustrate the methods of the high dynamic range receiver circuit as disclosed in US 2007-0084288 by Thomas as they relate to the present disclosure. An analog test signal from a single element probe is driven through four parallel gain circuits and digitization blocks to produce four different representations of the original signal: HDR_ANALOG[0] 401 (a very high gain version of the original signal), HDR_ANALOG[1] 402 (a high gain version of the original signal), HDR_ANALOG[2] 403 (a low gain version of the original signal), and HDR_ANALOG[3] 404 (a very low gain version of the original signal). All four of these new signals are driven through Assembly Node 405, where the most useful data from each of the signals 401, 402, 403, and 404 are combined to form a single high dynamic range representation of the original signal 406.

Figure 5:
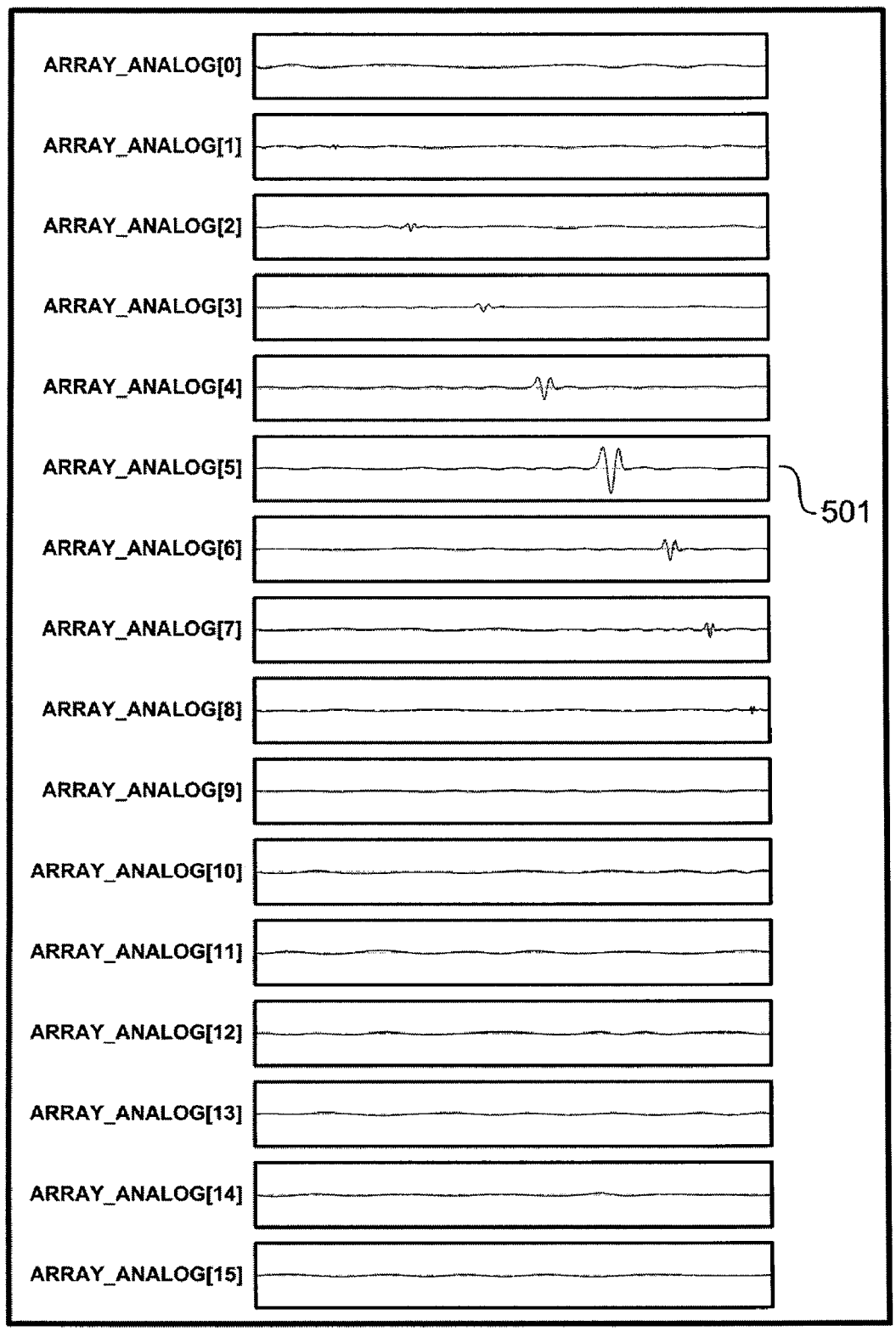
FIG. 5 is a waveform diagram illustrating a typical set of test signals received from an NDI array probe.

FIG. 5 is also provided for reference and illustrates a set of typical analog signals taken from a sixteen element array probe. Each of the sixteen elements provides a different analog signal 501 which must be digitized and precisely phase aligned so that analysis of the structure under test can be performed. The details of such analysis should be well-known to those skilled in the art.

FIGS. 6A and 6B graphically represent the interleaving sampling process used with the single element probe input as described in the discussion of the preferred embodiment of the present disclosure (illustrated in FIG. 2) and the first alternate embodiment of the present disclosure (illustrated in FIG. 3) respectively. For the four phase interleaving process of the preferred embodiment (represented by FIG. 6A), each analog signal (HDR_ANALOG[n]) is sampled four times by analog to digital converters driven with clock signals which are phase shifted with respect to each other by one quarter of the clock period. This results in four sets of data samples 601, 602, 603, and 604, which are combined to form a single digital representation of the original signal 605, effectively sampled at four times the analog to digital converters' clock frequency.

For the dual phase interleaving of the first alternate embodiment (represented by FIG. 6B), each analog signal (HDR_ANALOG[n]) is sampled twice by analog to digital converters driven with clock signals phase shifted with respect to each other by half the clock period. This results in two set of data samples 606 and 607, which are combined to form a single digital representation of the original signal, effectively sampled at twice the analog to digital converters' clock frequency.

FIG. 7 is a timing diagram illustrating the interleaving process described in the preferred embodiment of the present disclosure. It should be noted that the fine phase adjustments to the analog to digital clock signals used for the signal propagation delay compensation process (as described in detail in the discussion of FIG. 2) have been ignored in this diagram for clarity. The analog signal HDR_ANALOG[n] 701 represents one of the four signals generated from the single element probe input. The sixteen analog to digital converter clock signals are each driven with one of four clock phases 702, 703, 704, and 705 such that all four of the analog to digital converters digitizing any one of the analog signals (HDR_ANALOG[n]) will be driven with a different clock phase. In this way, the analog signal 701 is sampled four times per clock cycle.

FIG. 8 is a timing diagram illustrating the interleaving process described in the first alternate embodiment of the present disclosure illustrated in FIG. 3. As with FIG. 7, the fine phase adjustments of the signal propagation delay compensation process have been ignored for clarity. The analog signal HDR_ANALOG[n] 801 represents one of the four signals generated from the single element probe input. The eight analog to digital converter clock signals are each driven with one of two clock phases 802 and 803 such that both of the analog to digital converters driven by any one of the analog signals (HDR_ANALOG[n]) will be driven with a different clock phase. In this way, the analog signal 801 is sampled twice per clock cycle.

Figure 9:
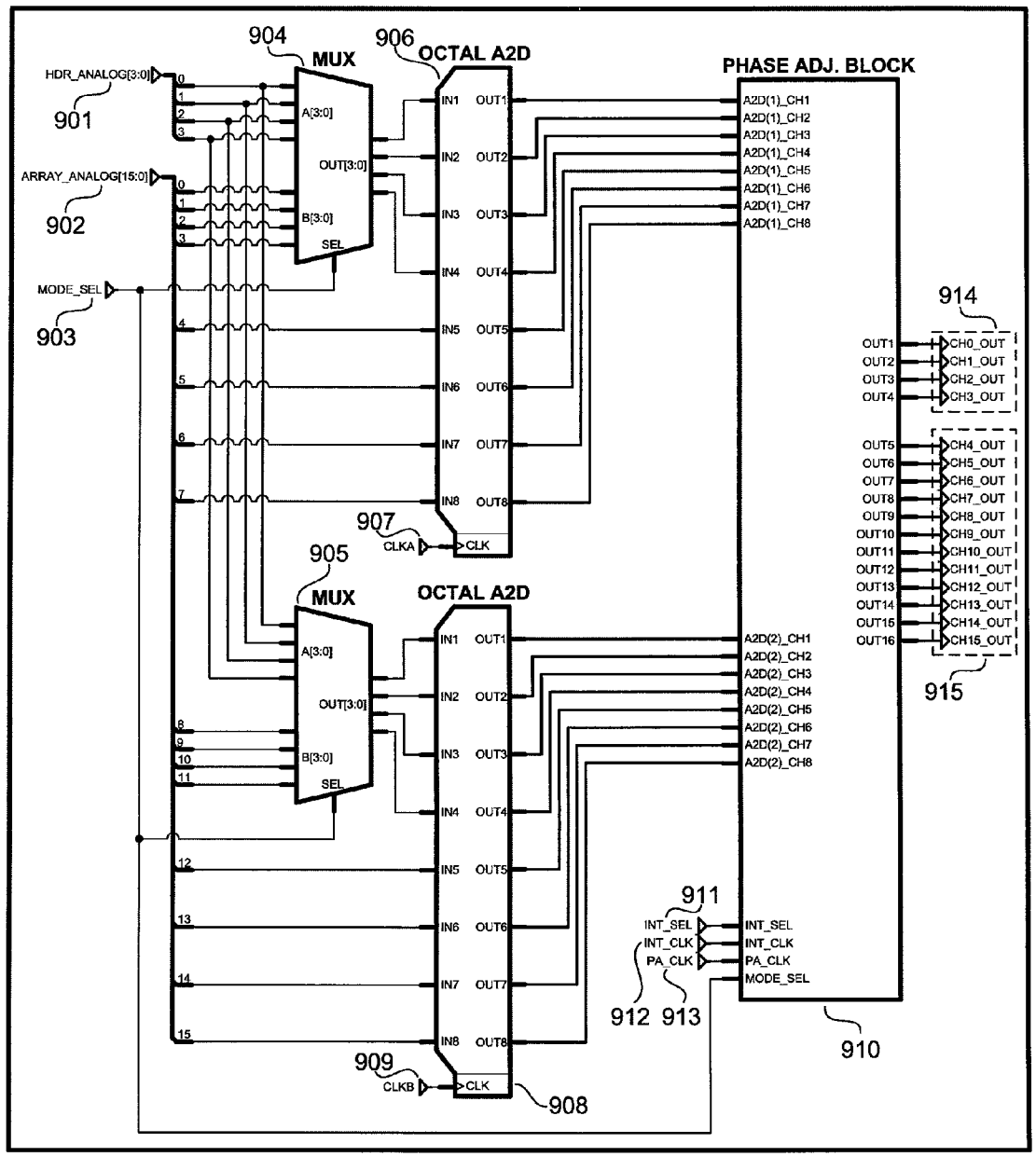
FIG. 9 is a top level block diagram of a second alternate embodiment of the multiple mode digitization system of the present disclosure.

FIG. 9 illustrates the block diagram of a second alternate embodiment of the present disclosure. This embodiment is well suited to an NDI instrument design which, for a variety of possible reasons well-known to those skilled in the art, must limit signal routing and layout complexity. It should be noted that while this second alternate embodiment, as illustrated in FIG. 9 and discussed below, realizes a specific digitization system suitable for use with two distinct inputs, the present disclosure is not limited in this regard. As with the preferred and first alternate embodiment, it should be apparent from the following discussion that the techniques and methods of the second alternate embodiment can be used to realize a plurality of multiple mode digitization systems well suited for use in an NDI instrument.

The two octal analog to digital converters 906 and 908 as presented in FIG. 9 are eight channel analog to digital conversion devices typical of what is available on the market as of the filing of the present disclosure. These single chip devices comprise eight individual analog to digital converters, all of which are driven by a single clock signal (CLKA 907 in the case of the first analog to digital converter 906 or CLKB 909 in the case of the second analog to digital converter 908). Devices of this type are particularly useful for designs which require a plurality of analog to digital converters to be used within a compact electronic device. Indeed, it will be shown in the ensuing discussion of the second alternate embodiment (illustrated in FIG. 9) that the methods of the present disclosure can be adapted to make use of such devices to realize a physically compact form of the multiple mode digitization system of the present disclosure.

As in the preferred and first alternate embodiments (illustrated in FIGS. 2 and 3, respectively), two sets of signals, HDR_ANALOG[3:0] 901 and ARRAY_ANALOG[15:0] 902, are provided to the multiple mode digitization system. The four signals from the HDR_ANALOG[3:0] input 901 are provided to the first input (labeled A[3:0]) of both multiplexers 904 and 905. Four of the signals from the second input, ARRAY_ANALOG[15:0] 902, are driven into the second input (labeled B[3:0]) of the first multiplexer 904 and another four signals from said input are driven into the second input (labeled B[3:0]) of the second multiplexer 905. The remaining eight signals of the array input 902 are provided directly to the octal analog to digital converters 906 and 908.

With this arrangement, when the single element mode is selected the four analog signals from the HDR_ANALOG[3:0] 901 input will be provided to the first four inputs of both of the octal analog to digital converters 906 and 908. Conversely, when the array probe mode is selected the first eight analog signals from the ARRAY_PROBE[15:0] input 902 will be provided to the first analog to digital converter 906, and the remaining eight signals will be provided to the second analog to digital converter 908. It should be noted that when the single element probe is selected, only four of the eight outputs of each octal analog to digital converter 906 and 908 will provide meaningful data, as only their corresponding inputs will be responsive to valid analog input signals. The eight channels not used by analog to digital converters 906 and 908 when in single element mode are kept in a low power or power off mode by means of control signals (not shown).

In the array probe mode—when the signals from the ARRAY_ANALOG[15:0] input 902 are selected—CLKA 907 and CLKB 909 are driven at the desired sampling frequency and in phase with respect to each other. This results in all sixteen of the ARRAY_ANALOG[15:0] input signals 902 being sampled simultaneously and their corresponding digital representations then provided to the Phase Adjustment Block 910. In single element probe mode—when the signals from the HDR_ANALOG[3:0] input 901 are selected—CLKA 907 and CLKB 909 are driven at the desired sampling frequency but 180 degrees out of phase with respect to each other. This allows the two octal analog to digital converters 906 and 908—each of which are digitizing the same four analog input signals (HDR_ANALOG[3:0]) 901—to perform a two way interleaved sampling process identical to that discussed in the first alternate embodiment and illustrated in FIGS. 6B and 8. In this mode, each pair of digitized signals—each analog signal in the HDR_ANALOG[3:0] input 901 is digitized twice, producing two digital signals sampled 180 degrees apart—is provided to the Phase Adjustment Block 910 which combines them into a single, higher bandwidth signal (with twice the effective sample rate) and provides phase adjustment as required.

Thus, when array probe mode is selected by the MODE_SEL control 903, the sixteen analog signals are digitally sampled in parallel, phase adjusted, and provided to the outputs of the multiple mode digitization system 914 and 915. Conversely, when the single element probe mode is selected, the four analog signals are digitally sampled through an interleave process (resulting in digital signals with an effective sample rate of twice the frequency of the CLKA 907 and CLKB 908 clock signals), phase adjusted, and provided to the first bank of outputs 914. In single element probe mode, the second bank of outputs 915 contains no meaningful data.

While the phase offset between the two clock signals 907 and 909 is sufficient to provide the interleaved sampling operation required by the present disclosure, without a plurality of phase adjustable clocks the propagation delay compensation operation—which can be critical in many NDI signal processing systems—must be realized in another way. In the second embodiment of the present disclosure, these individual signal phase adjustments are performed by a plurality of programmable digital finite impulse response (FIR) filters located inside the Phase Adjustment Block 910.

U.S. Pat. No. 3,997,772 by Crochiere discloses a digital phase shifter which uses an FIR filter with memory loaded coefficients to provide phase adjustments to digital signals in increments less than the sampling rate of said digital signals. The method taught by Crochiere has become a standard practice in digital signal processing, and the details of using such a technique to phase delay a digital signal should be well-known to those skilled in the art.

Figure 10:
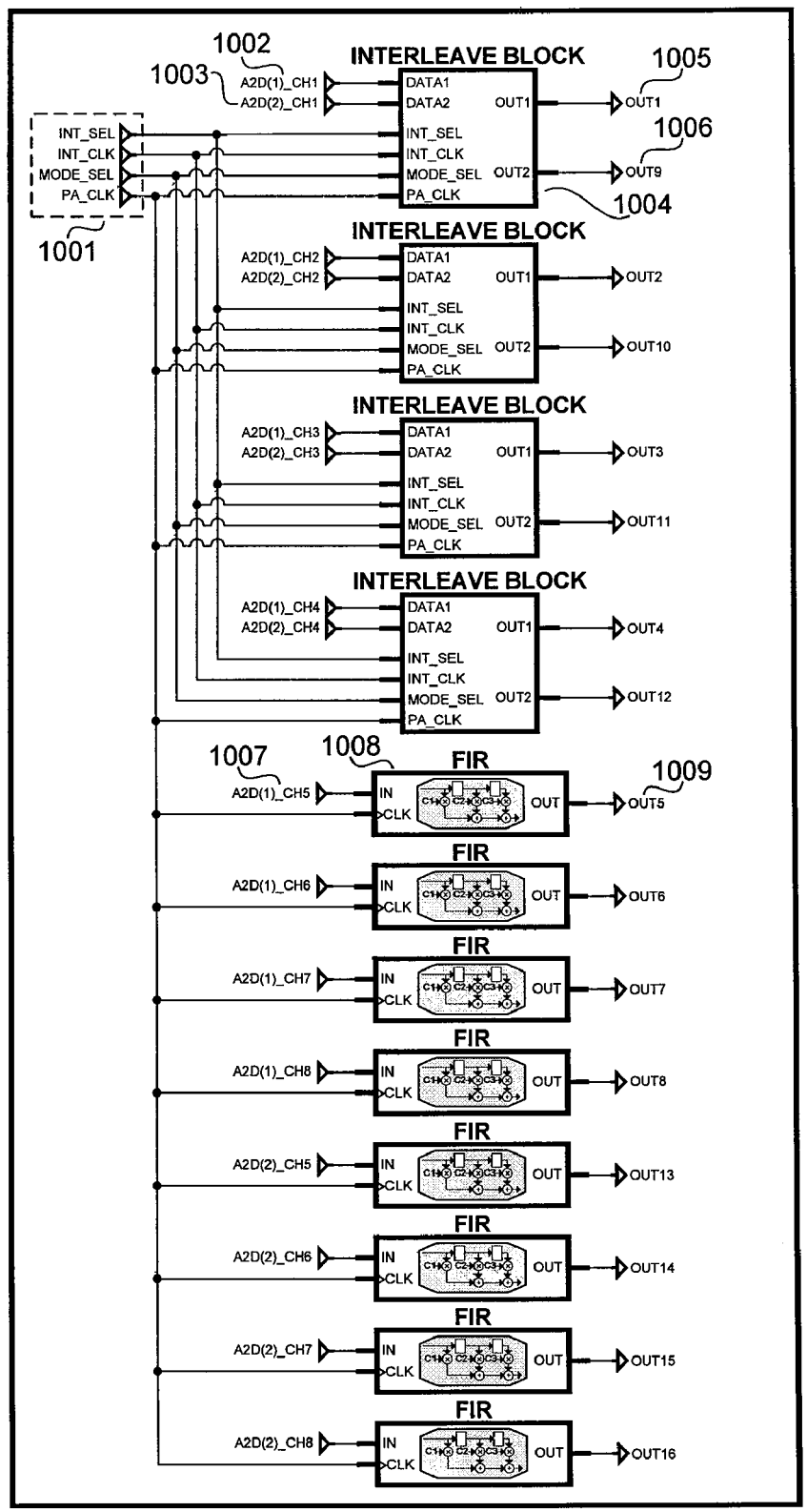
FIG. 10 is a block diagram illustrating the Phase Adjustment Block used in the second alternate embodiment.

FIG. 10 illustrates the block diagram of the Phase Adjustment Block (910 in FIG. 9). Four Interleave Blocks 1004 are responsive to the first four digital signals from each octal analog to digital converter (906 and 908 in FIG. 9). The remaining eight signals—which are used only in array probe mode, and thus are never used for interleaved sampling—are provided directly to digital programmable FIR filters 1008 built in the manner taught by Crochiere.

Looking to the first Interleave Block 1004, the first digitized signal from each analog to digital converter 1002 and 1003 are provided to the two data inputs of the block. In single element mode, these two signals will each represent a digitized version—each sampled 180 degrees apart—of the first analog signal of the single element input (901 in FIG. 9). Using the bank of control signals 1001 provided, the Interleave Block 1004 combines these two signals into one signal with twice the effective sample rate (as previously discussed and detailed in FIGS. 6B and 8), phase adjusts the resulting signal through a programmable digital FIR (located inside the Interleave Block 1004), and provides the resulting digital signal to the first output 1005. In single element probe mode, the second output 1006 contains no meaningful data.

In array probe mode the two data signals 1002 and 1003 provided to the first Interleave Block 1002 represent digitized versions of the first and ninth analog signals provided by the array probe input (902 in FIG. 9) respectively. In this mode, the bank of control signals 1001 configure the Interleave Block 1004 to bypass the interleaving circuitry and provide each of the data signals 1002 and 1003 to a separate programmable digital FIR filter (located inside the Interleave Block 1004). The signals produced from said FIR filters are then provided to the two outputs 1005 and 1006. In this mode the programmable digital FIR filters 1008 are driven with a clock signal (provided from the bank of control signals 1001) with the same frequency and phase as the sample clocks (CLKA 907 and CLKB 909 of FIG. 9) such that the remaining eight digitized signals (those not provided to Interleave Blocks 1004) are phase adjusted as required.

Figure 11:
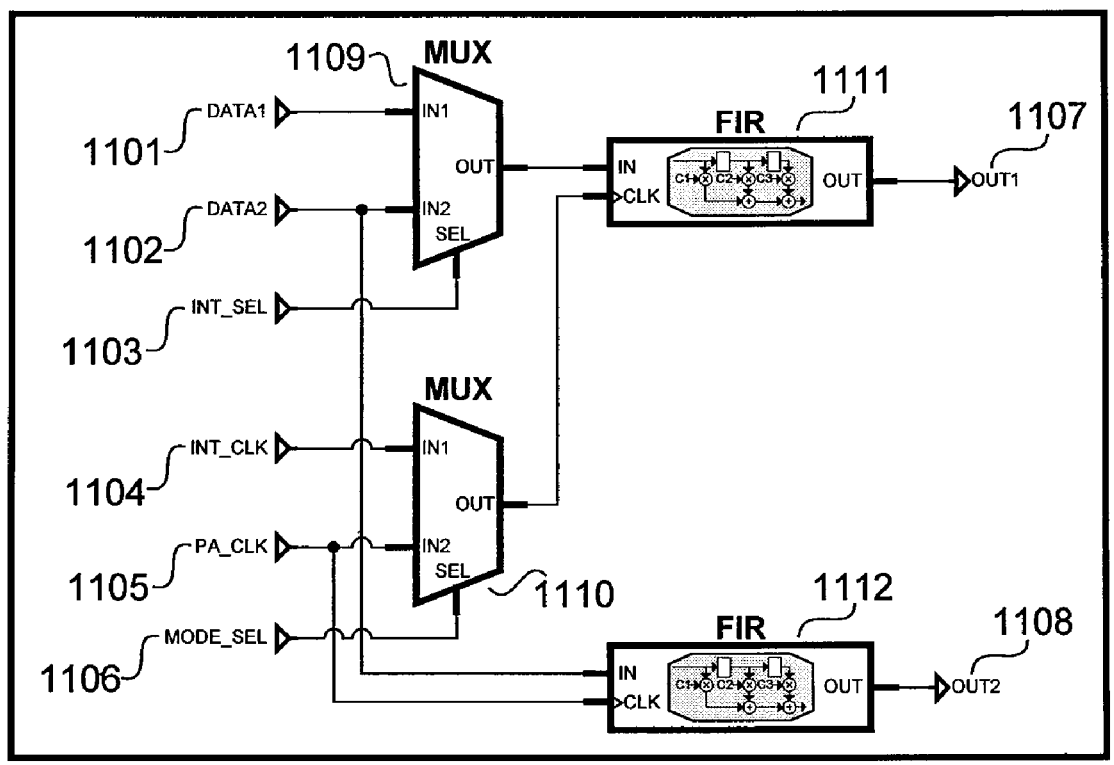
FIG. 11 is a block diagram illustrating the Interleave Block used in the second alternate embodiment.
Figure 12A:
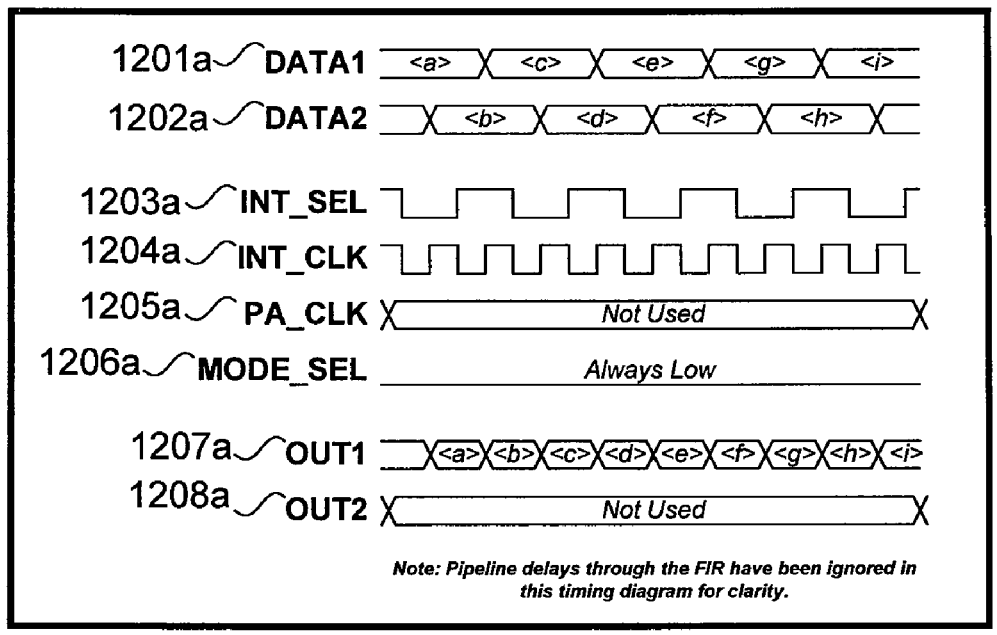
FIG. 12A is a timing diagram illustrating the input, control, and output signals used within the second alternate embodiment in single element mode.
Figure 12B:
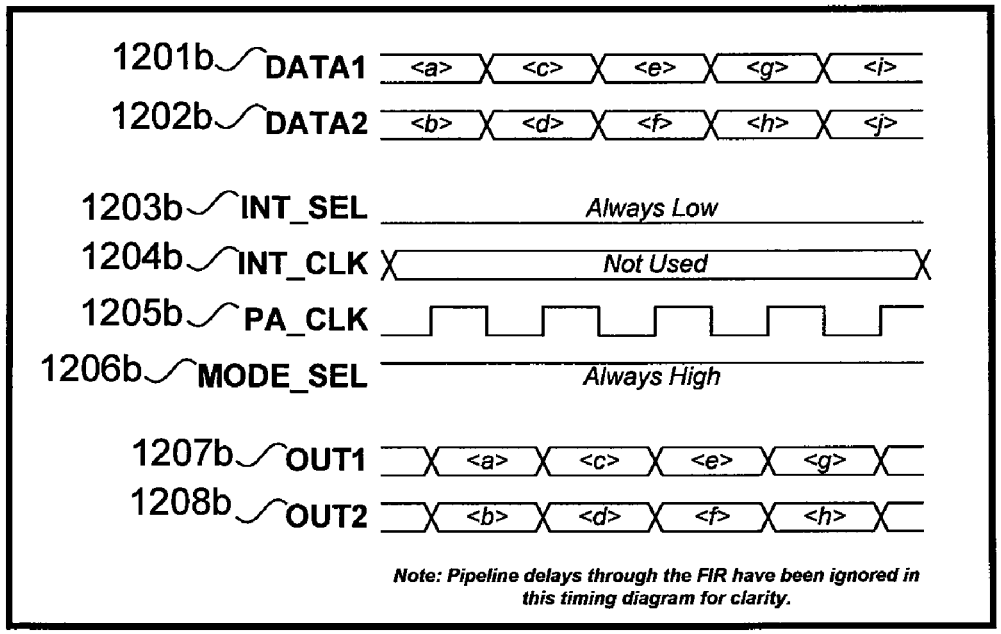
FIG. 12B is a timing diagram illustrating the input, control, and output signals used within the second alternate embodiment in array probe mode.

FIG. 11 illustrates the block diagram of the Interleave Block referenced in FIG. 10. FIGS. 12A and 12B are timing diagrams which illustrate the input, control, and output signals associated within the Interleave Block referenced in FIG. 10 used in the single element probe mode and array probe mode respectively. Taken together, these three figures illustrate the use and function of Interleave Block both in single element probe mode and array probe mode.

In single element probe mode, two digital signals 1101/1201*a* and 1102/1202*a* are provided to the first multiplexer 1109. As shown in FIG. 12A, these two data signals have been sampled with clock signals 180 degrees out of phase. The second multiplexer 1110—controlled by the MODE_SEL control 1106/1206*a*—selects between two clock signals INT_CLK 1104/1204*a* and PA_CLK 1105/1205*a* and provides the result to the clock input of the first digital programmable FIR filter 1111. In single element probe mode, the INT_CLK input 1104/1204*a* is always selected. INT_CLK 1104/1204*a* provides a clock signal with twice the frequency of the original sample rate of the data signals and is used to drive the programmable digital FIR filter 1111. INT_SEL 1103/1203*a* is used to control the first multiplexer 1109 and is driven such that the multiplexer 1109 will alternate between its inputs before every rising edge of INT_CLK 1104/1204*a*. In this way, the two digital input signals 1101/1201*a* and 1102/1202*a* will be interleaved into a single digital signal, which is subsequently phase adjusted through the first FIR filter 1111 and provided to the first output 1107/1207*a*. It should be noted that in this mode, no signal is driven on the PA_CLK input 1105/1205*a* and the second FIR filter provides no meaningful data to the second output 1108/1208*a*.

In array probe mode, two digital signals 1101/1201*b* and 1102/1202*b* are provided to the first multiplexer 1109. The second data signal 1102/1202*b* is also provided directly to the second programmable digital FIR filter 1112. As shown in FIG. 12B, these two data signals have been sampled with clock signals of the same frequency and phase. The second multiplexer 1110—controlled by the MODE_SEL control 1106/1206*b*—selects between two clock signals INT_CLK 1104/1204*b* and PA_CLK 1105/1205*b* and provides the result to the clock input of the first digital programmable FIR filter 1111. In array probe mode, the PA_CLK input 1105/1205*b* is always selected and provides a clock signal with the same frequency and phase of the original sample clock. In this mode, PA_CLK 1105/1205*b* is also used to drive the second programmable digital FIR filter 1112. INT_SEL 1103/1203*a* is used to control the first multiplexer 1109 and is driven such that said multiplexer 1109 will always select the first input signal 1101/1201*b*. In this way, the two digital input signals 1101/1201*b* and 1102/1202*b* will each be provided to a separate programmable digital FIR filter, subsequently phase adjusted, and the resulting digital signals provided to the outputs 1107/1207*b* and 1108/1208*b*.

It should be noted that the clock signal selection multiplexer 1110 shown in FIG. 11 is intended as a conceptual element to illustrate the function of Interleave Block with as much clarity as possible. Long established methods of routing clock signals in the manner shown in FIG. 11 and disclosed in the preceding discussion—such as deselecting gates or clock enable signals—should be well-known to those skilled in the art.

While the preceding discussion and the illustration in FIGS. 9 and 10 depict a multiple mode digitization system similar in function to the first alternate embodiment, it should be obvious from the preceding discussion that the methods of the second alternate embodiment can be used to realize a system—one comprising four octal analog to digital converters instead of two—similar in function to the preferred embodiment. Indeed, it should be noted that the methods of the present disclosure can be used to provide any level of interleaved sampling required by an NDI instrument design.

The methods of the second alternate embodiment represent a trade-off with respect to the primary and first alternate embodiment. While the bank of programmable FIR filters (most likely realized by, but not limited to, an FPGA or a dedicated digital signal processor) adds complexity to the digital signal processing design and will likely require additional software considerations for an NDI instrument design, it greatly reduces the design challenge of routing a plurality of high frequency clock signals. Aside from the obvious challenges of physically finding room for and routing so many critical signals on a printed circuit board, timing errors caused by clock jitter, phase delay, and other sources are greatly reduced.

It should also be noted that while the multiple mode digitization system of the present disclosure is well suited to respond to the analog signals from a plurality of probe types, the structure of the second alternate embodiment (as illustrated in FIG. 9) is especially well suited for use with a phased array probe.

Figure 13:
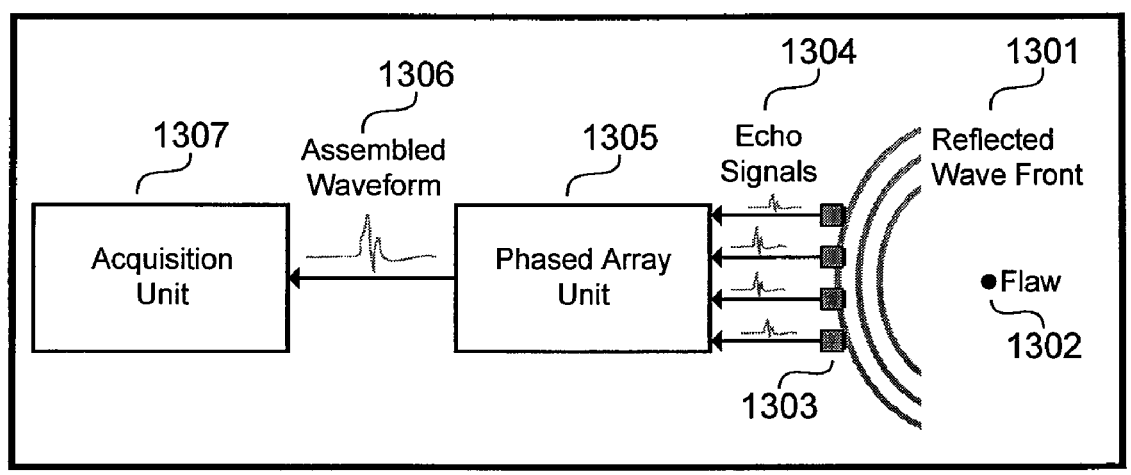
FIG. 13 is a diagram briefly illustrating the function of a phased array receiver (sometimes referred to as a beamformer) as it relates to the present disclosure.

FIG. 13 illustrates a block diagram of a typical NDI phased array receiver. Acoustic energy reflects off of a flaw 1302 in a structure under test and impacts an array of transducers 1303 in the form of a reflected wave front 1301. This reflected wave front 1301 meets each of the transducers in the array 1303 at a different time interval, resulting in a plurality of echo signals 1304. A phased array unit 1305 (often referred to as a beamformer or a phased array receiver module), along with filtering, digitizing, and amplifying the echo signals 1304, must time delay and amplitude scale each of the echo signals 1304 according to the focal laws used to construct the original test wave front. This delay and scaling operation is typically performed with programmable FIR filters in the manner taught by Crochiere in U.S. Pat. No. 3,997,772. The principles of NDI phased array inspection, including the derivation and application of focal laws, should be well-known to those skilled in the art.

The programmable FIR filters used in the second alternate embodiment (illustrated in FIGS. 9 and 10) are well suited to be used for the delay and scaling operations required for focal law signal adjustments critical to a phased array inspection process, while at the same time performing their original intended purpose of compensating for signal propagation delay. While not limited to such an instrument, the second alternate embodiment is especially well suited for use with an NDI instrument with at least one phased array probe input.

A third alternate embodiment is now described that applies to FIGS. 1, 2, 3, 9, and 10. It is advantageous for the NDI instrument of the present disclosure to have provisions to be used with a variety of multi-element array probe types (FIG. 1 102) of different frequencies and element (channel) counts. Array probes of higher frequencies typically have smaller elements which enables the probe design to be optimization for inspection application geometries that require it.

As described supra and depending on the embodiment, the sampling rate of the analog to digital converters when a multi-element array probe 102 is selected as the input will be either one half or one quarter of the sampling rate used when single element probe 101 is selected as the input.

The third alternate embodiment provides the capability to increase the simultaneous sampling rate of multi-element array probe 102. For example, the simultaneous sampling rate of a multi-element array probe can be increased by a binary integer factor for a number of probe elements equal to the quotient of the total number of analog to digital converters in Digitization System 105 divided by said factor. Exemplary embodiments of double sampling rate (factor of 2) and quadruple sampling rate (factor of 4) are provided below. It should be noted that a system according to the third embodiment need not necessarily increase the sampling rate by a binary integer factor, but that increase in the sampling rate by other factors would also be within the scope of a system according to the third embodiment.

Referring to FIG. 2, the NDI instrument of an exemplary third alternate embodiment is comprised of sixteen channels. For the case when an eight or less channel version of multi-element array probe 102 is connected and the double sampling rate mode is selected, only the eight, or less, analog signals from array probe input (ARRAY_ANALOG[15:0]) 202 are wired to sixteen channel multiplexer's 204 inputs such that each analog signal is provided to two analog to digital converters 206 with their respective clock signals 207 180 degrees out of phase with one another.

It should be noted that a greater than eight channel version of multi-element array probe 102 (e.g. sixteen channels) may be connected when the double sampling rate mode is selected. In this case, all sixteen analog signals from array probe input (ARRAY_ANALOG[15:0]) 202 are wired to sixteen channel multiplexer's 204 inputs such that each analog signal from eight or less channels may be provided to two analog to digital converters 206 with their respective clock signals 207 180 degrees out of phase with one another.

All channels are can be sampled at the double sampling rate if done so in two successive simultaneous digitization cycles. For the example of 16 channel multi-element array probe 102, sixteen channel multiplexer 204 would provide the first group of eight channels for simultaneous sampling, followed next by the second group of eight channels for simultaneous sampling. The resulting data from the said two successive sampling events are then combined to form a single set of data representing the signals from all sixteen channels sampled at the double sampling rate.

For the case when a four or less channel version of multi-element array probe 102 is connected and the quadruple sampling rate mode is selected, only the four or less analog signals from array probe input (ARRAY_ANALOG[15:0]) 202 are wired to sixteen channel multiplexer's 204 inputs such that each analog signal is provided to four analog to digital converters 206 with their respective clock signals 207 90 degrees out of phase with one another.

It should be noted that a greater than eight channel version of multi-element array probe 102 (e.g. sixteen channels) may be connected when the quadruple sampling rate mode is selected. In this case, all sixteen analog signals from array probe input (ARRAY_ANALOG[15:0]) 202 are wired to sixteen channel multiplexer's 204 inputs such that each analog signal from four or less channels may be provided to four analog to digital converters 206 with their respective clock signals 207 90 degrees out of phase with one another.

All channels can be sampled at the quadruple sampling rate if done so in four successive simultaneous digitization cycles. For the example of 16 channel multi-element array probe 102, sixteen channel multiplexer 204 would provide the first group of four channels for simultaneous sampling, followed next by the second group of four channels for simultaneous sampling, then the third group of four channels for simultaneous sampling, and lastly the forth group of four channels for simultaneous sampling. The resulting data from the said four successive sampling events are then combined to form a single set of data representing the signals from all sixteen channels sampled at the quadruple sampling rate.

The method for doubling the sample rate of the four analog signals from single element probe (HDR_ANALOG[3:0]) 901 (FIG. 9) described for the second alternate embodiment applies also to this third alternate embodiment, except for the following:

a) the analog signals provided to the output of multiplexers 904 and 905 of FIG. 9 are selected from array probe input (ARRAY_ANALOG[15:0]) 902, not HDR_ANALOG[3:0] 901;

b) the addition of four Interleave Blocks 1004 to FIG. 10 for signals 1007 currently provided to FIR's 1008. The first, second, third, and fourth additional Interleave Blocks 1004 would have as their data 1 and 2 inputs A2D(1)_CH5 and A2D(2)_CH5, A2D(1)_CH6 and A2D(2)_CH6, A2D(1)_CH7 and A2D(2)_CH7, and A2D(1)_CH8 and A2D(2)_CH8, respectively. Bank of control signals 1001 would be connected in the same way as the four Interleave Blocks 1004 as shown in FIG. 10.

c) the removal of FIR's 1008 from FIG. 10.

It should be noted that while the third alternate embodiment, as described above, realizes a specific digitization system suitable for use to double the sampling rate, the present disclosure is not limited in this regard. As with the preferred and the first and second alternate embodiments, it should be apparent from the description of the third alternate embodiment that its techniques and methods can be used to realize a plurality of multiple mode digitization systems well suited for use in an NDI instrument—e.g. quadrupling the sampling rate.

Although the present invention has been described in relation to particular embodiments thereof, many other variations and modifications and other uses will become apparent to those skilled in the art. It is preferred, therefore, that the present invention not be limited by the specific disclosure herein.

What is claimed is:

1. A testing instrument system for testing objects non-destructively with analog signal waves, selectively using a single element probe or an array probe, the testing instrument comprising:

an interface for receiving a plurality of analog inputs from the array probe, and for receiving a single analog input associated with the single element probe;

a scaling amplifier network configured to receive the single analog input and to produce therefrom a plurality of differently scaled representations of the single analog input;

a multiplexer including a plurality of input terminals sufficient to receive the plurality of analog inputs and the plurality of scaled representations of the single analog input, and including a plurality of multiplexer output channels, the multiplexer being effective to output a selected group of the signals presented at the input terminals thereof;

a plurality of analog to digital converters (ADCs) coupled to the multiplexer output channels to produce corresponding digital signals, the plurality of analog to digital converters being sufficient in number to allow simultaneous allocation of a respective analog to digital converter to each of the plurality of analog signals associated with the array probe;

a mode selector coupled to the multiplexer and configured to cause the multiplexer to selectively couple to its multiplexer output channels of a selected group of the signals provided at its input terminals; and a control circuit which is effective to cause the respective outputs of the ADCs to provide at least one of the digital magnitudes of the plurality of analog signals and a high dynamic digital representation of the single analog input, wherein the high dynamic digital representation of the single analog input is provided in a form of a digital output which has a bit resolution greater than that available from any single one of the ADCs, by utilizing a plurality of said ADCs for processing said single analog input.

2. The system of claim 1, wherein the mode selector is configured to select one of said probes.

3. The system of claim 1, further comprising a phase adjuster to adjust respective phases of said digital signals.

4. The system of claim 3, wherein said phase adjuster is capable of adjusting each phase within 360 degrees.

5. The system of claim 1, wherein each analog to digital converter is driven with a respective clock.

6. The system of claim 1, wherein said analog to digital converters are driven with a common clock.

7. The system of claim 1, wherein at least one of said probes includes only one sensor.

8. The system of claim 1, wherein at least one of said probes includes a plurality of sensors.

9. The system of claim 8, wherein a number of said channels are equal in number to a number of said plurality of sensors.

10. The system according to claim 8, wherein the plurality of input sensors comprise a plurality of input sensors of a non-destructive inspection instrument.

11. The system of claim 8, wherein a number of said channels are less than a number of said plurality of sensors.

12. The system of claim 1, wherein said system is capable of interleaving said digital signals.

13. The system of claim 1, wherein said system is capable of a plurality of sampling rates.

14. The system of claim 1, wherein said interface is configured to received inputs for at least one of said array probe, said single element probe, and a high bandwidth, high dynamic range probe.

15. The system of claim 1, wherein at least one of said probes includes a single sensor capable of producing one analog signal which is distributed to multiple channels.

16. The system of claim 1, wherein at least one of said probes includes a plurality of sensors each capable of producing a respective analog signal which is received by a respective channel.

17. The system according to claim 1, wherein each of the plurality of analog to digital converters is driven according to a unique, independent clock signal.

18. The system according to claim 17, wherein each unique, independent clock signal allows for phase adjustments less than a predetermined sample period.

19. The system according to claim 18, further comprising a plurality of programmable finite impulse response filters operative to phase delay the respective digitized signal output from the analog to digital converter.

20. The system according to claim 17, wherein at least one of the probe signals is supplied to more than one analog to digital converter, whereby a phase adjustment among the more than one analog to digital converters achieves a higher sample rate within the predetermined sample period.

* * * * *